United States Patent
Vaughan (10) Patent No.: US 9,474,592 B1
(45) Date of Patent: Oct. 25, 2016

(54) BARBED SLEEVE FOR USE IN MEDICAL PROCEDURES

(71) Applicant: Roderick Andrew Vaughan, Murfreesboro, TN (US)

(72) Inventor: Roderick Andrew Vaughan, Murfreesboro, TN (US)

(*) Notice: Subject to any disclaimer, the term of this patent is extended or adjusted under 35 U.S.C. 154(b) by 0 days.

(21) Appl. No.: 15/042,513

(22) Filed: Feb. 12, 2016

Related U.S. Application Data (60) Provisional application No. 62/241,226, filed on Oct. 14, 2015.

(51) Int. Cl.
*A61F 2/08* (2006.01)

(52) U.S. Cl.
CPC .......... *A61F 2/0811* (2013.01); *A61F 2/08* (2013.01); *A61F 2002/0864* (2013.01); *A61F 2002/0882* (2013.01); *A61F 2002/0888* (2013.01); *A61F 2210/0004* (2013.01); *A61F 2220/0016* (2013.01); *A61F 2220/0025* (2013.01); *A61F 2220/0033* (2013.01); *A61F 2230/0006* (2013.01); *A61F 2230/0069* (2013.01); *A61F 2230/0086* (2013.01); *A61F 2250/0007* (2013.01); *A61F 2250/0025* (2013.01); *A61F 2250/0026* (2013.01)

(58) Field of Classification Search
CPC ........ A61F 2/08; A61F 2/0811; A61F 2/848; A61F 2002/0817; A61F 2002/0823; A61F 2002/0829; A61F 2002/0835; A61F 2002/0841; A61F 2002/0847; A61F 2002/0852; A61F 2002/0858; A61F 2002/0864; A61F 2002/087; A61F 2002/0876; A61F 2002/0882; A61F 2002/0888; A61F 2002/0894; A61F 2002/8483; A61F 17/0487; A61F 2017/0412; A61F 2017/0427; A61F 2017/0429; A61F 2017/043; A61F 2017/0432; A61F 2017/0433; A61F 2017/0435; A61F 2017/0437; A61F 2017/0454; A61F 2017/0403; A61F 2017/044; A61F 2017/0445; A61F 2017/045; A61F 2017/0456; A61F 2017/0461

See application file for complete search history.

(56) References Cited

U.S. PATENT DOCUMENTS

| | | |
|---|---|---|
| 72,093 A | 12/1867 | Shaw |
| 698,247 A | 4/1902 | Bernhard et al. |
| 843,507 A | 2/1907 | Villalaz |
| 1,245,099 A | 10/1917 | Gross et al. |
| 2,099,950 A | 11/1937 | Whitehead et al. |
| 3,221,746 A | 12/1965 | Noble |

(Continued)

FOREIGN PATENT DOCUMENTS

| | | | | |
|---|---|---|---|---|
| BE | WO 2013139985 A2 | * | 9/2013 | ......... A61B 17/0401 |
| FR | WO 2008053128 A9 | * | 6/2009 | ......... A61B 17/0487 |

(Continued)

OTHER PUBLICATIONS

IDC& Co Barrel Lock Wristband (available at https://www.idcband.com/security-wristbands/fabric-wristbands/fabric-barrel-lock?qty=1000) (last accessed Jan. 26, 2016).

(Continued)

*Primary Examiner* — Andrew Iwamaye
(74) *Attorney, Agent, or Firm* — Shane V. Cortesi (57) ABSTRACT

A sleeve with interior barbs that are designed to grasp a tissue and fix the tissue to a body part such as a bone are described. Optionally, the sleeve exterior surface includes a fastener configured to fix the sleeve relative to the body part. Optionally, the wall of the sleeve includes a plurality of wall holes. Methods of using the barbed sleeve in surgery are also described.

14 Claims, 7 Drawing Sheets

(56) References Cited

U.S. PATENT DOCUMENTS

| | | | |
|---|---|---|---|
| 4,263,904 A | | 4/1981 | Judet |
| 5,108,431 A | * | 4/1992 | Mansat ............... A61F 2/0811 623/13.14 |
| 5,201,598 A | | 4/1993 | Tehan |
| 5,250,048 A | | 10/1993 | Gundolf |
| 5,372,599 A | * | 12/1994 | Martins ............. A61B 17/0401 606/232 |
| 5,391,173 A | * | 2/1995 | Wilk ................. A61B 17/0469 128/898 |
| 5,425,766 A | * | 6/1995 | Bowald ................ A61L 27/58 623/13.18 |
| 5,456,721 A | * | 10/1995 | Legrand ............... A61F 2/0805 623/1.5 |
| 5,505,735 A | * | 4/1996 | Li ....................... A61F 2/0811 606/232 |
| 5,632,748 A | * | 5/1997 | Beck, Jr. ............... A61F 2/0811 606/232 |
| 5,669,935 A | * | 9/1997 | Rosenman ......... A61B 17/0487 606/151 |
| 6,645,226 B1 | * | 11/2003 | Jacobs ................. A61B 17/064 606/215 |
| 7,201,773 B2 | | 4/2007 | Steiner et al. |
| 8,062,363 B2 | | 11/2011 | Hirpara et al. |
| 8,747,469 B2 | | 6/2014 | Wang et al. |
| 8,900,302 B2 | * | 12/2014 | Gonzalez-Hernandez ........... A61F 2/0811 623/13.15 |
| 2001/0049530 A1 | * | 12/2001 | Culbert .................. A61B 17/68 606/63 |
| 2002/0055780 A1 | * | 5/2002 | Sklar .................... A61F 2/0811 623/13.12 |
| 2003/0187444 A1 | * | 10/2003 | Overaker ........... A61B 17/0401 606/232 |
| 2003/0191530 A1 | * | 10/2003 | Sklar .................... A61F 2/0811 623/13.14 |
| 2004/0087955 A1 | | 5/2004 | Bordi |
| 2005/0143734 A1 | * | 6/2005 | Cachia .................. A61B 17/68 606/60 |
| 2005/0197699 A1 | | 9/2005 | Jacobs et al. |
| 2005/0245932 A1 | * | 11/2005 | Fanton ............... A61B 17/0401 606/232 |
| 2006/0089525 A1 | * | 4/2006 | Mamo ................ A61B 17/0401 600/37 |
| 2006/0089711 A1 | * | 4/2006 | Dolan .............. A61B 17/00234 623/2.37 |
| 2009/0157193 A1 | | 6/2009 | McKay |
| 2009/0234451 A1 | * | 9/2009 | Manderson ........ A61B 17/8645 623/13.14 |
| 2011/0288566 A1 | * | 11/2011 | Kubiak ..................... A61F 2/08 606/151 |
| 2013/0060333 A1 | * | 3/2013 | Gonzalez-Hernandez ........... A61F 2/0811 623/13.15 |
| 2013/0090731 A1 | * | 4/2013 | Walker ............... A61B 17/0401 623/13.14 |
| 2014/0296979 A1 | * | 10/2014 | Delfosse ............ A61B 17/0401 623/13.12 |
| 2014/0379004 A1 | * | 12/2014 | Raybin ................ A61B 17/083 606/143 |
| 2015/0289866 A1 | * | 10/2015 | Bowen .................. A61F 2/0811 606/232 |

FOREIGN PATENT DOCUMENTS

| | | | | |
|---|---|---|---|---|
| NZ | WO 2006062419 A1 | * | 6/2006 | ........... A61B 17/842 |
| WO | WO 9210149 A1 | * | 6/1992 | ............ A61F 2/0811 |

OTHER PUBLICATIONS

Jianxin Gift & Accessory Co. Ltd. Plastic One-way Sliding Lock for Wristbands (available at jxband.manufacturer.globalsources.com/si/6008840730884/pdtl/promotional-woven/1060434308/wristbands.html) (last accessed Oct. 14, 2015).

\* cited by examiner

BARBED SLEEVE FOR USE IN MEDICAL PROCEDURES

RELATED APPLICATIONS

This application claims priority under 35 USC 119 to U.S. Provisional Application No. 62/241,226, filed Oct. 14, 2015, the contents of which are incorporated herein by reference in their entirety.

BACKGROUND

1. Technical Field

The present invention relates to a sleeve with interior barbs that are configured to, for example, grasp a body tissue and fix the body tissue to another body part such as a bone.

2. Background of the Invention

ACL (anterior cruciate ligament) and other surgeries require the attachment of tissue to bone.

In the prior art, it is known to secure tissue to a bone by placing tissue into a hole in the bone and then placing an interference screw adjacent to the tissue within the hole. Interference screws are sold by, for example, Arthex, Inc., Naples, Fla. Unfortunately, the tissue may loosen from the hold of the interference screw within the bone. Pressure placed upon the tissue by the screw may also result in tissue necrosis, poor in growth of healing tissue, and poor revascularization of the tissue, all of which may compromise or limit the integrity of the tissue and contribute to failure, necessitating further surgery. Placement of an interference screw within the hole also displaces the tissue to the side of the hole, thereby placing the tissue in an eccentric position within the hole and contributing to imprecise positioning of the tissue. An endo-button device may also be used to secure tissue to bone; however, this provides only a single point of fixation and the point of fixation is remote from the tissue.

Thus, there is a need for more biologically optimal and precise way to fixate tissue to bone in ACL and other surgeries.

BRIEF SUMMARY

The present disclosure provides a barbed sleeve and methods of using the same as described herein.

In some embodiments, the present disclosure provides a method of attaching a tissue to a bone of an animal comprising:

a) creating a hole in the bone;

b) providing a barbed sleeve comprising a sleeve interior, a sleeve exterior, a sleeve wall separating the sleeve interior from the sleeve exterior and comprising a wall interior surface facing the sleeve interior and a wall exterior surface, a sleeve front end comprising a sleeve front opening leading to the sleeve interior, a sleeve rear end comprising a sleeve rear opening leading to the sleeve interior, a sleeve length extending from the sleeve front end to the sleeve rear end, a sleeve width perpendicular to the sleeve length, a plurality of interior barbs comprising a front end extending from the sleeve wall, a rear end located in the sleeve interior, and a length extending from the front end of the interior barb to the rear end of the interior barb, wherein the barbed sleeve is comprised of a biocompatible material;

c) positioning the barbed sleeve into the hole in the bone;

d) providing a tissue having a front end and a rear end; and e) positioning the rear end of the tissue through the sleeve front end and into the sleeve interior, wherein the plurality of interior barbs are configured to allow the tissue to move rearwardly within the sleeve interior and further wherein the plurality of interior barbs are configured to prevent the tissue from moving forwardly within the sleeve interior.

Optionally, prior to step e) the tissue's front end is already attached to an adjacent body part of the animal. For example, using a ligament as an example of the tissue, prior to step e) the ligament may be torn at the rear end (so that it is not attached to the bone containing the sleeve) and the opposing front end may be attached to an adjacent bone and step e) may involve positioning the torn rear end of the ligament through the sleeve front end and into the sleeve interior so as to re-attach/repair the torn rear end to the bone using the sleeve. Alternatively, using a tendon as an example of the tissue, prior to step e) the tendon may be torn at the rear end and the opposing front end may remain attached to an adjacent muscle and step e) may involve positioning the torn rear end of the tendon through the sleeve front end and into the sleeve interior so as to re-attach/repair the torn rear end to the bone using the sleeve. In other embodiments, prior to step e), the tissue's front end may not already be attached to an adjacent body part of the animal and the method may further include a subsequent step of attaching the tissue's front end to the adjacent body part.

Optionally, prior to positioning the tissue into the sleeve interior, the tissue comprises a tissue length extending from the tissue front end to the tissue rear end and a tissue width perpendicular to the tissue length, wherein said plurality of interior barbs comprise at least one pair of interior barbs whose rear ends are located approximately 180 degrees apart and at approximately the same distance from the sleeve front end (e.g., diametrically opposed interior barbs) and further wherein said rear ends of said at least one pair create a space that has a width that is less than the tissue width. Optionally, the barbed sleeve comprises multiple such pairs spaced about the sleeve perimeter and about the sleeve length (e.g., multiple rows of diametrically opposed interior barbs, with each row having more than one pair of diametrically opposed interior barbs). In other embodiments, the interior barbs may be irregularly spaced about the sleeve perimeter such that no interior barbs are located approximately 180 degrees apart.

Optionally, the tissue is a tendon. Optionally, the tendon is a tendon graft. Optionally, the tissue is a ligament. Optionally, the tissue is a graft. Optionally, the graft is a synthetic graft. Optionally, step e) comprises using sutures to pull the tissue rearwardly within the sleeve interior. Optionally, step e) comprises pushing the tissue rearwardly within the sleeve interior. Optionally, the barbed sleeve is generally cylindrical in shape and comprises a sleeve circumference, and further wherein the plurality of interior barbs are spaced about the sleeve circumference (in addition to the sleeve length). Optionally, the barbed sleeve is oblong in shape and the plurality of interior barbs are spaced about the sleeve perimeter (in addition to the sleeve length). Optionally, the sleeve wall comprises a plurality of wall holes extending from the wall interior surface to the wall exterior surface, the plurality of wall holes configured to allow vascularization and tissue growth. Optionally, each of the plurality of wall holes is located directly next to an interior barb, and further wherein the interior barb is integral with the sleeve wall. Optionally, each wall hole is substantially the same shape and optionally the same size as the interior barb directly next to the wall hole. Optionally, the sleeve length is from about 5 mm to about 50 mm and the sleeve width is from about 5 mm to about 30 mm. Optionally, the sleeve length is larger than the sleeve width. Optionally, the interior barbs are angled between approximately 10 degrees and 80 degrees relative to the sleeve length. Optionally, the interior barbs have an interior barb width perpendicular to the interior barb length and further wherein the rear ends of the interior barbs have a tapered width. Optionally, the wall exterior surface comprises a fastener configured to fix the barbed sleeve relative to the bone. Optionally, the fastener is a flange located adjacent to the sleeve rear end and further wherein after step c), the flange is configured to prevent the sleeve rear end from moving through the hole in the bone. Optionally, after step c), the hole in the bone has a hole width parallel to the sleeve width and the flange has a flange width parallel to the sleeve width and further wherein the hole width is less than the flange width. Optionally, the flange comprises a flange width, and further wherein the flange width is not perpendicular to the sleeve width and further wherein the flange width is not perpendicular to the sleeve length. In other embodiments, the flange width may be generally perpendicular to the sleeve length. Optionally, the fastener comprises threads located on the wall exterior surface. Optionally, the sleeve front end comprises at least one slot and the method further comprises inserting a screwdriver into the at least one slot and turning the screwdriver and the barbed sleeve to fix the barbed sleeve to the bone. Optionally, the fastener comprises a plurality of exterior barbs comprising a rear end extending from the wall, a front end and located in the sleeve exterior, and a length extending from the front end of the exterior barb to the rear end of the exterior barb. Optionally, the hole in the bone of step a) and the barbed sleeve are generally cylindrical in shape. Optionally, the hole in the bone of step a) comprises a bone hole diameter and the barbed sleeve comprises a sleeve diameter and further wherein the bone hole diameter is equal to or greater than the sleeve diameter. Optionally, at least some of the plurality of interior barbs are curved. Optionally, at least some of the plurality of interior barbs are straight. Optionally, the hole in the bone extends partially through the bone. Optionally, the hole in the bone extends completely through the bone. Optionally, the bone forms part of a joint. Optionally, the plurality of interior barbs and the sleeve wall are comprised of the same material. Optionally, the barbed sleeve is comprised of a biocompatible material selected from the group consisting of a biological material, a biocomposite material, metal and a polymeric material.

In still further embodiments, the present disclosure provides a barbed sleeve configured to be fixed to a bone comprising: a sleeve interior configured to hold a tissue, a sleeve exterior, a sleeve wall separating the sleeve interior from the sleeve exterior and comprising a wall interior surface facing the sleeve interior and a wall exterior surface, a sleeve front end comprising a sleeve front opening leading to the sleeve interior, a sleeve rear end comprising a sleeve rear opening leading to the sleeve interior, a sleeve length extending from the sleeve front end to the sleeve rear end, a sleeve width perpendicular to the sleeve length, a plurality of interior barbs comprising a front end extending from the sleeve wall, a rear end located in the sleeve interior, and a length extending from the front end of the interior barb to the rear end of the interior barb, wherein the barbed sleeve is comprised of a biocompatible material, wherein the exterior surface of the wall comprises threads configured to fix the barbed sleeve relative to a bone, wherein the plurality of interior barbs are configured to allow the tissue to move rearwardly within the sleeve interior, and further wherein the plurality of interior barbs are configured to prevent the tissue from moving forwardly within the sleeve interior. The barbed sleeve may further include one or more of the features described above with respect to the method, including without limitation, the cylindrical or oblong shape, spacing of the interior barbs, alternating lengths of the interior barbs, wall holes, sleeve length and sleeve width, the shape of the interior barbs, and the material forming the interior barbs and sleeve wall.

In still further embodiments, the present disclosure provides a barbed sleeve configured to be fixed to a bone comprising: a sleeve interior configured to hold a tissue, a sleeve exterior, a sleeve wall separating the sleeve interior from the sleeve exterior and comprising a wall interior surface facing the sleeve interior and a wall exterior surface, a sleeve front end comprising a sleeve front opening leading to the sleeve interior, a sleeve rear end comprising a sleeve rear opening leading to the sleeve interior, a sleeve length extending from the sleeve front end to the sleeve rear end, a sleeve width perpendicular to the sleeve length, a plurality of interior barbs comprising a front end extending from the sleeve wall, a rear end located in the sleeve interior, and a length extending from the front end of the interior barb to the rear end of the interior barb, wherein the barbed sleeve is comprised of a biocompatible material, wherein the exterior surface of the wall comprises a fastener configured to fix the barbed sleeve relative to a bone, wherein the plurality of interior barbs are configured to allow the tissue to move rearwardly within the sleeve interior, and further wherein the plurality of interior barbs are configured to prevent the tissue from moving forwardly within the sleeve interior. The barbed sleeve may further include one or more of the features described above with respect to the method, including without limitation, the cylindrical or oblong shape, spacing of the interior barbs, alternating lengths of the interior barbs, wall holes, sleeve length and sleeve width, the shape of the interior barbs, and the material forming the interior barbs and sleeve wall.

In still further embodiments, the present disclosure provides a barbed sleeve configured to be fixed to a bone comprising: a sleeve interior configured to hold a tissue, a sleeve exterior, a sleeve wall separating the sleeve interior from the sleeve exterior and comprising a wall interior surface facing the sleeve interior and a wall exterior surface, a sleeve front end comprising a sleeve front opening leading to the sleeve interior, a sleeve rear end comprising a sleeve rear opening leading to the sleeve interior, a sleeve length extending from the sleeve front end to the sleeve rear end, a sleeve width perpendicular to the sleeve length, a plurality of interior barbs comprising a front end extending from the sleeve wall, a rear end located in the sleeve interior, and a length extending from the front end of the interior barb to the rear end of the interior barb, wherein the barbed sleeve is comprised of a biocompatible material, wherein the exterior surface of the wall comprises a flange located adjacent to the rear end of the barbed sleeve and configured to fix the barbed sleeve relative to a bone, the flange having a flange width parallel to the barbed sleeve width, wherein the flange width is greater than the barbed sleeve width, wherein the plurality of interior barbs are configured to allow the tissue to move rearwardly within the sleeve interior, and further wherein the plurality of interior barbs are configured to prevent the tissue from moving forwardly within the sleeve interior. The barbed sleeve may further include one or more of the features described above with respect to the method, including without limitation, the cylindrical or oblong shape, spacing of the interior barbs, alternating lengths of the interior barbs, wall holes, sleeve length and sleeve width, the shape of the interior barbs, and the material forming the interior barbs and sleeve wall.

In still further embodiments, the present disclosure provides a barbed sleeve configured to be fixed to a bone comprising: a sleeve interior configured to hold a tissue, a sleeve exterior, a sleeve wall separating the sleeve interior from the sleeve exterior and comprising a wall interior surface facing the sleeve interior and a wall exterior surface, a sleeve front end comprising a sleeve front opening leading to the sleeve interior, a sleeve rear end comprising a sleeve rear opening leading to the sleeve interior, a sleeve length extending from the sleeve front end to the sleeve rear end, a sleeve width perpendicular to the sleeve length, a plurality of interior barbs comprising a front end extending from the sleeve wall, a rear end located in the sleeve interior and pointing toward the sleeve rear end, and a length extending from the front end of the interior barb to the rear end of the interior barb, wherein the barbed sleeve is comprised of a biocompatible material, wherein the barbed sleeve comprises a sleeve circumference/perimeter, wherein the plurality of interior barbs are spaced about the sleeve circumference/perimeter, wherein adjacent circumferentially- or perimeter-spaced barbs have different lengths, wherein the plurality of interior barbs are configured to allow the tissue to move rearwardly within the sleeve interior, and further wherein the plurality of interior barbs are configured to prevent the tissue from moving forwardly within the sleeve interior. The barbed sleeve may further include one or more of the features described above with respect to the method, including without limitation, the fasteners, wall holes, sleeve length and sleeve width, the shape of the interior barbs, and the material forming the interior barbs and sleeve wall.

In still further embodiments, the present disclosure provides a barbed sleeve configured to be fixed to a bone comprising: a sleeve interior configured to hold a tissue, a sleeve exterior, a sleeve wall separating the sleeve interior from the sleeve exterior and comprising a wall interior surface facing the sleeve interior and a wall exterior surface, a sleeve front end comprising a sleeve front opening leading to the sleeve interior, a sleeve rear end comprising a sleeve rear opening leading to the sleeve interior, a sleeve length extending from the sleeve front end to the sleeve rear end, a sleeve width perpendicular to the sleeve length, a plurality of interior barbs comprising a front end extending from the sleeve wall, a rear end located in the sleeve interior and pointing toward the sleeve rear end, and a length extending from the front end of the interior barb to the rear end of the interior barb, wherein the barbed sleeve is comprised of a biocompatible material, wherein the wall comprises a plurality of exterior barbs configured to fix the barbed sleeve relative to a bone, each exterior barb comprising a rear end extending from the wall, a front end pointing toward the sleeve front end and located in the exterior, and a length extending from the front end of the barb to the rear end of the barb, wherein the plurality of interior barbs are configured to allow the tissue to move rearwardly within the sleeve interior, and further wherein the plurality of interior barbs are configured to prevent the tissue from moving forwardly within the sleeve interior. The barbed sleeve may further include one or more of the features described above with respect to the method, including without limitation, the cylindrical or oblong shape, spacing of the interior barbs, alternating lengths of the interior barbs, wall holes, sleeve length and sleeve width, the shape of the interior barbs, and the material forming the interior barbs and sleeve wall.

In still further embodiments, the present disclosure provides a barbed sleeve configured to be fixed to a bone comprising: a sleeve interior configured to hold a tissue, a sleeve exterior, a sleeve wall separating the sleeve interior from the sleeve exterior and comprising a wall interior surface facing the sleeve interior and a wall exterior surface, a sleeve front end comprising a sleeve front opening leading to the sleeve interior, a sleeve rear end comprising a sleeve rear opening leading to the sleeve interior, a sleeve length extending from the sleeve front end to the sleeve rear end, a sleeve width perpendicular to the sleeve length, a plurality of interior barbs comprising a front end extending from the sleeve wall, a rear end located in the sleeve interior and pointing toward the sleeve rear end, and a length extending from the front end of the interior barb to the rear end of the interior barb, wherein the barbed sleeve is comprised of a biocompatible material, wherein the plurality of interior barbs are spaced about the perimeter/circumference of the barbed sleeve, wherein the wall comprises a plurality of wall holes extending from the wall interior surface to the wall exterior surface, the plurality of wall holes spaced about the barbed sleeve perimeter/circumference and about the length of the barbed sleeve, the plurality of wall holes configured to allow vascularization and tissue growth, wherein the plurality of interior barbs are configured to allow the tissue to move rearwardly within the sleeve interior, and further wherein the plurality of interior barbs are configured to prevent the tissue from moving forwardly within the sleeve interior. The barbed sleeve may further include one or more of the features described above with respect to the method, including without limitation, alternating lengths of the interior barbs, the features of the wall holes, sleeve length and sleeve width, the shape of the interior barbs, and the material forming the interior barbs and sleeve wall.

BRIEF DESCRIPTION OF THE DRAWINGS

FIGS. 10 and 11 illustrate schematic views of the barbed sleeve of FIG. 8 positioned in the hole that has been drilled in a bone; FIG. 10 includes an access hole in the bone configured to allow sutures to pass therethrough.

FIG. 13 illustrates a side, cross-sectional view of a portion of the barbed sleeve of FIG. 1; in FIG. 13, only one side of the wall is shown.

FIG. 15 illustrates a side, cross-sectional view of a portion of a barbed sleeve of another embodiment of the present invention; in FIG. 15 opposing sides of the wall are shown.

in FIG. 18, the barbed sleeve is oblong.

DETAILED DESCRIPTION

With reference to FIGS. 1-18, the present invention provides a barbed sleeve designated by the numeral 10. In the drawings, not all reference numbers are included in each drawing for the sake of clarity.

Referring further to FIGS. 1-18 in some embodiments, the barbed sleeve 10 includes a sleeve interior 28, a sleeve exterior 29, a sleeve wall 30 separating the sleeve interior 28 from the sleeve exterior 29 and comprising a wall interior surface 32 facing the sleeve interior 28 and a wall exterior surface 34, a sleeve front end 36 comprising a sleeve front opening 38 leading to the sleeve interior 28, a sleeve rear end 40 comprising a sleeve rear opening 42 leading to the sleeve interior 28, a sleeve length 44 extending from the sleeve front end 36 to the sleeve rear end 40, a sleeve width 46 perpendicular to the sleeve length 44, a plurality of interior barbs 48 comprising a front end/base 50 extending from the sleeve wall 30, a free rear end/tip 52 located in the sleeve interior 28 and a length 54 extending from the front end 50 of the interior barb 48 to the rear end 52 of the interior barb 48. The free rear end/tip 52 of each respective interior barb 48 is rearwardly disposed relative to the front end/base 50 of the same interior barb 48 (relative to the sleeve length 44) and points toward the sleeve rear end 40.

The barbed sleeve 10 is comprised of a biocompatible material. Optionally, the barbed sleeve 10 is comprised of biocomposite material, metal or a polymeric material, such as a thermoplastic polymer such as polylactide and polyglycolide, calcium hydroxyapatite and/or collagen.

Figure 6:
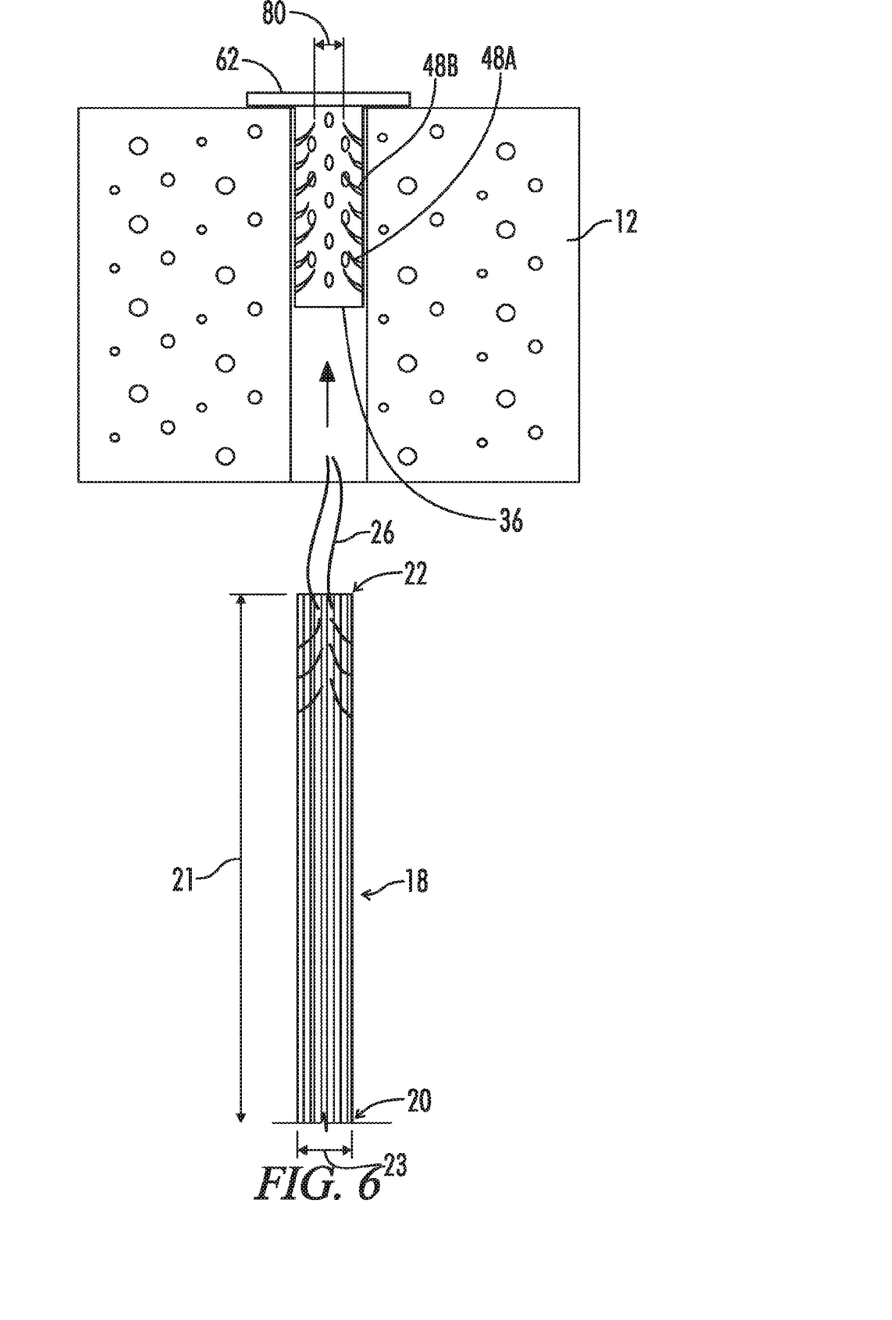
FIGS. 6-7 illustrate schematic views of a tendon being inserted through the barbed sleeve of FIG. 3.
Figure 7:
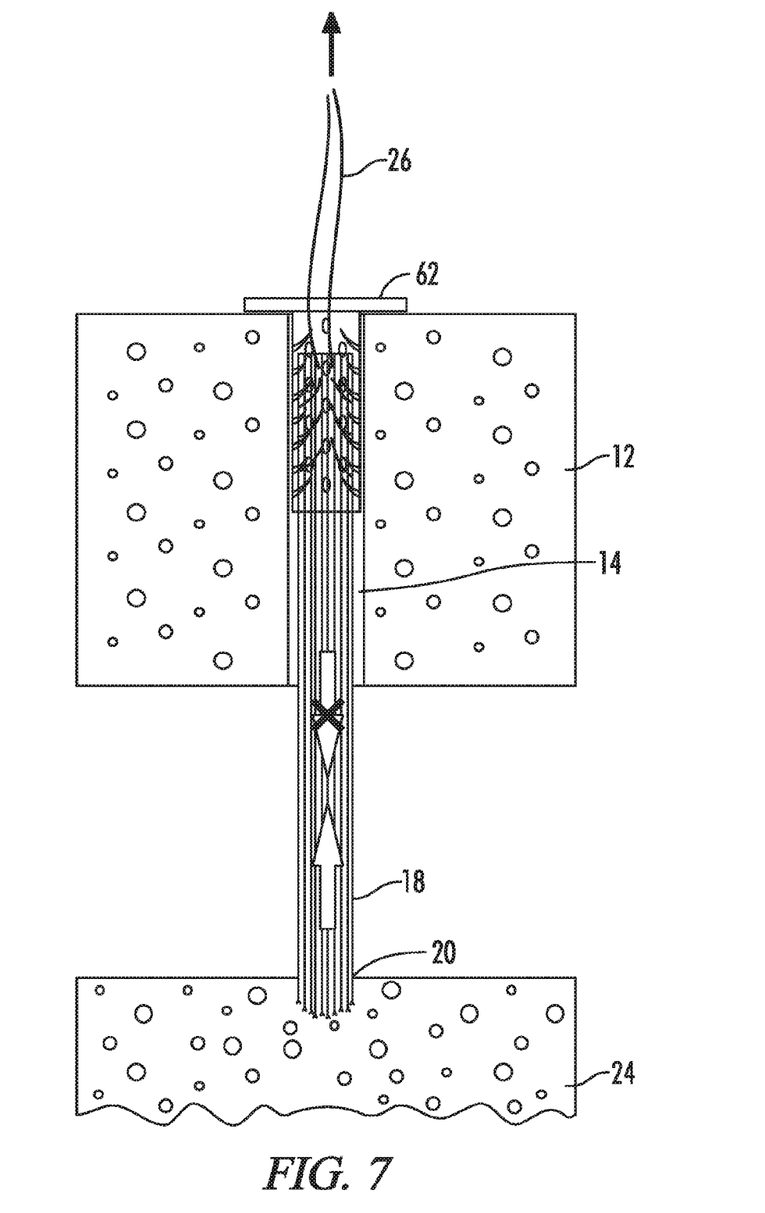

The barbed sleeve 10 is designed to be placed in a hole 14 located in animal (e.g., human) bone 12, as shown in FIGS. 1, 3, 6-8, 10 and 11. (The hole 14 is also referred to herein as the bone hole 14). The interior barbs 48 are designed to allow a tissue 18 to move through the sleeve front end 36 and toward the sleeve rear end 40. However, once the tissue 18 is in the sleeve interior 28, the interior barbs 48 engage the tissue 18 and prevent the tissue 18 from moving forwardly within the sleeve interior 28. In other words, the interior barbs 48 allow the tissue 18 to move in one direction (rearwardly) and prevent the tissue 18 from moving out the sleeve front end 36, as illustrated in FIG. 7. As a result, the barbed sleeve 10 anchors the tissue 18 to the bone 12. As shown in the drawings, preferably all of the interior barbs 48 point in the same direction—i.e., towards the sleeve rear end 40—and the front end/base 50 of each interior barb 48 (which extends from the wall 30) is located forwardly relative to the rear end/tip 52 of the same interior barb 48. In some embodiments, the rear end/tip 52 of each interior barb 48 moves/deflects toward the sleeve wall 30 and/or the tissue 18 deforms as the tissue 18 enters the sleeve interior 28 and contacts the interior barbs 48, as indicated by the 8 symbol in FIG. 13. Optionally, the interior barbs 48 purchase the tissue 18 as the tissue 18 enters the sleeve interior 28 and contacts the interior barbs 48.

Figure 18:
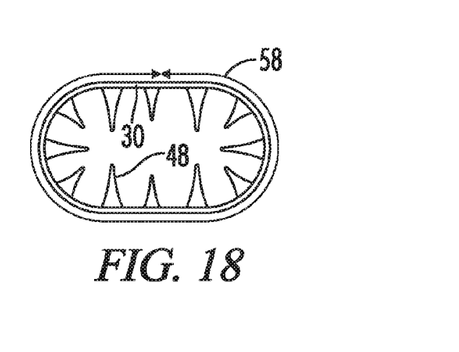
FIG. 18 illustrates a front, plan view of a barbed sleeve of another embodiment of the present invention.

The dimensions of the sleeve 10 and the dimensions and arrangements of interior barbs 48 should be chosen based on the width/diameter of the tissue 18 so that the tissue 18 engages the interior barbs 48 when the tissue 18 is positioned in the sleeve interior 28. More particularly, with reference to FIG. 15, where the barbed sleeve 10 is cylindrical, the barbed sleeve 10 has an inner diameter 82, the interior barbs 48 are spaced equally about the circumference 58 of the barbed sleeve 10, and the rear ends 52 of diametrically opposed interior barbs 48 protrude inwardly a distance 84 to leave a space between the rear ends 52 of diametrically opposed interior barbs 48 that has a width/diameter 80 that is calculated by taking the inner diameter 82 and subtracting the distance 84 that each diametrically opposed interior barb 48 protrudes inwardly. The tissue 18 in such a case has a width/diameter 23 that is less than the width/diameter 80 of the space. The width/diameter 80 of the space between the rear ends 52 of diametrically opposed interior barbs 48 may be uniform along the sleeve length 44. If the sleeve 10 is oblong as shown in FIG. 18, for example, the rear ends 52 of interior barbs 48 that are located on opposing sides of the barbed sleeve 10 will likewise leave a space having a width 80.

Optionally, the tissue 18 has a tissue rear end 22 that is located in the sleeve interior 28 and a tissue front end 20 that is attached to a body part 24 of the animal adjacent to the bone 12 so that the tissue 18 extends from the body part 24 to the bone 12. The tissue 18 includes a tissue length 21 extending from the tissue rear end 22 to the tissue front end 20 and a tissue width 23 perpendicular to the tissue length 21. Optionally, the tissue 18 is a tendon (e.g., a natural tendon or tendon graft) or a ligament. Optionally, the tissue 18 is a synthetic graft. Optionally, sutures 26 are used to pull the tissue 18 rearwardly within the sleeve interior 28, as best seen in FIG. 6. Preferably, the sutures 46 are attached adjacent—i.e., at or near—the rear end 22 of the tissue 18. In other embodiments, instead of sutures 46, the surgeon pushes the tissue 18 rearwardly within the sleeve interior 28.

Figure 1:
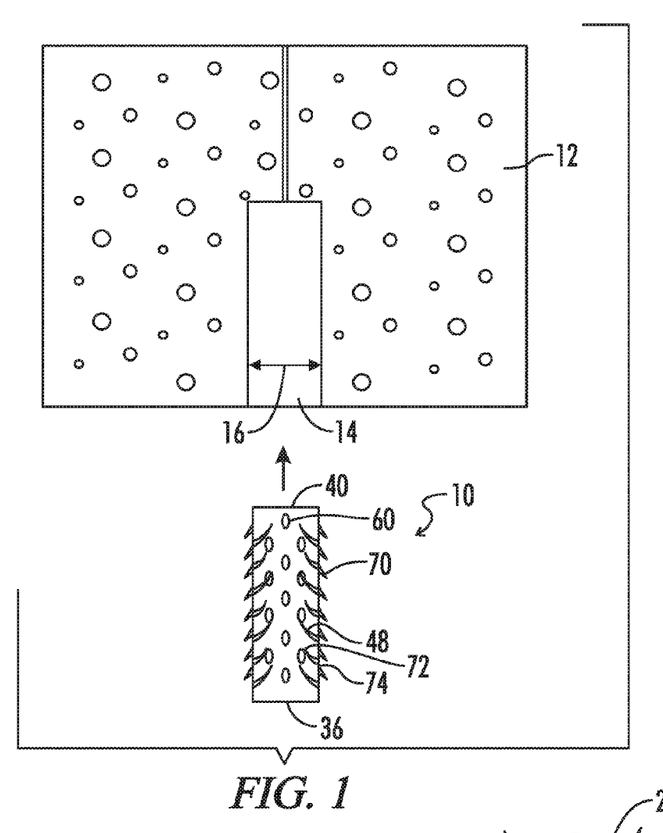
FIG. 1 illustrates a schematic view of a barbed sleeve of one embodiment of the invention being positioned in a hole that has been drilled in a bone; the barbed sleeve of FIG. 1 includes exterior barbs.
Figure 2:
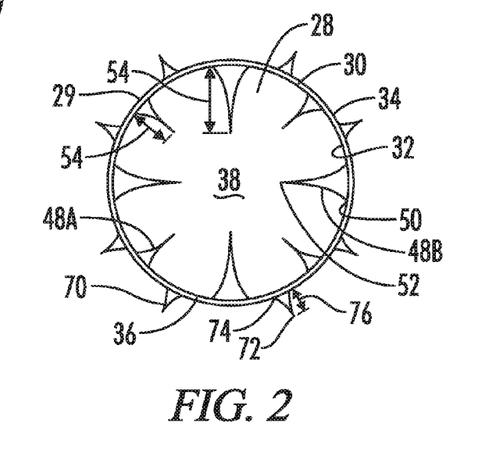
FIG. 2 illustrates a front, plan view of the barbed sleeve of FIG. 1.
Figure 3:
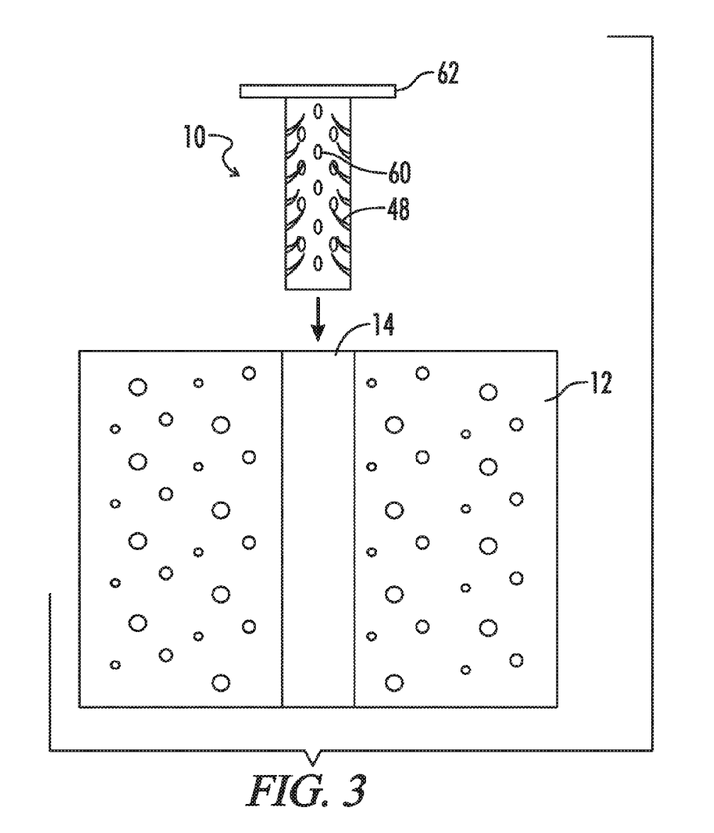
FIG. 3 illustrates a schematic view of a barbed sleeve of another embodiment of the invention being positioned in a hole that has been drilled in a bone; the barbed sleeve of FIG. 3 includes a flange located at the rear end of the barbed sleeve and configured to secure the barbed sleeve to the bone.
Figure 4:
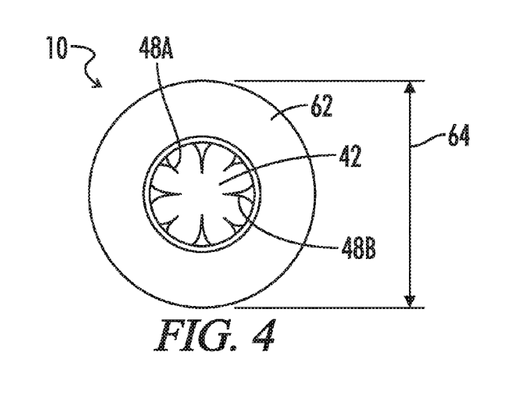
FIG. 4 illustrates a rear, plan view of the barbed sleeve of FIG. 3.
Figure 8:
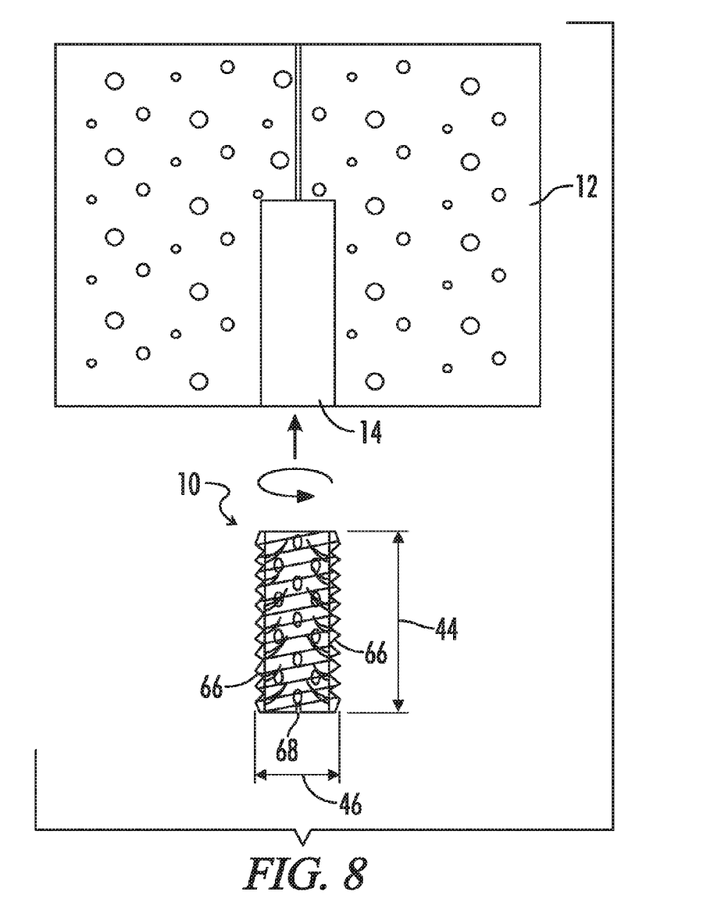
FIG. 8 illustrates a schematic view of a barbed sleeve of another embodiment of the invention being positioned in a hole that has been drilled in a bone; the barbed sleeve of FIG. 8 includes external threads configured to secure the barbed sleeve to the bone.
Figure 9:
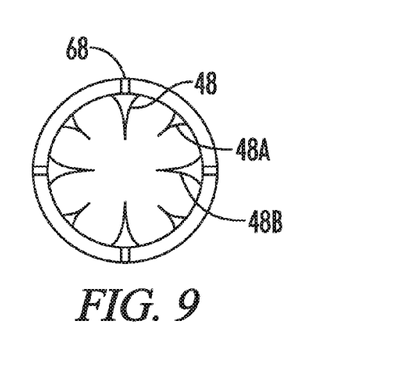
FIG. 9 illustrates a front, plan view of the barbed sleeve of FIG. 8.

In some embodiments, the barbed sleeve 10 is generally cylindrical in shape. In other embodiments, the barbed sleeve 10 may be oblong (as shown in FIG. 18) or another shape. Regardless of the shape, the plurality of interior barbs 48 may be spaced about a perimeter/circumference 58 of the barbed sleeve 10 and about the sleeve length 44. For example, in some embodiments where the plurality of interior barbs 48 are spaced about a perimeter/circumference 58 of the barbed sleeve 10, the barbed sleeve 10 may have adjacent interior barbs 48 at the exact same distance from the sleeve front end 36 and the barbed sleeve 10 may have several rows of interior barbs 48 along the sleeve length 44 as shown in, for example, FIGS. 1-12. In other embodiments where the plurality of interior barbs 48 are spaced about a perimeter/circumference 58 of the barbed sleeve 10, the plurality of interior barbs 48 may be offset so that adjacent interior barbs 48 are not at the exact same distance from the sleeve front end 36. Optionally, the plurality of interior barbs 48 are spaced substantially evenly about the sleeve perimeter/circumference 58. Optionally, adjacent perimeter/circumferentially-spaced interior barbs 48 have different lengths 54, as best seen in FIGS. 2, 4, and 9—i.e., the interior barbs 48 have alternating lengths 54, meaning that each short barb 48A is located between longer barbs 48B and each longer barb 48B is between two short barbs 48A). It will be appreciated that the barbed sleeve 10 may be in the shape of a tapered cylinder (i.e., a cylinder whose diameter 46 and circumference 58 gradually decrease from the front end 36 to the rear end 38) in which case the interior barbs 48 may be spaced substantially evenly about each circumference 58 along the sleeve length 44. However, a barbed sleeve in the shape of a cylinder with a constant diameter 46 and constant circumference 58, as shown in FIGS. 1, 3, 6, 8, 10-11, is preferred.

Optionally, the sleeve wall 30 comprises a plurality of wall holes 60 extending through the sleeve wall 30 (i.e., from the wall interior surface 32 to the wall exterior surface 34). As explained above, the barbed sleeve 10 may be cylindrical, oblong or another shape. Like the interior barbs 48, the plurality of wall holes 60 may be spaced about a perimeter/circumference 58 of the barbed sleeve 10 and about the sleeve length 44. For example, in some embodiments where the plurality of wall holes 60 are spaced about a perimeter/circumference 58 of the barbed sleeve 10, the barbed sleeve 10 may have adjacent wall holes 60 at the exact same distance from the sleeve front end 36 and the barbed sleeve 10 may have several rows of wall holes along the sleeve length 44. In other embodiments where the plurality of wall holes 60 are spaced about a perimeter/circumference 58 of the barbed sleeve 10, the plurality of wall holes 60 may be offset so that adjacent wall holes 60 are not at the exact same distance from the sleeve front end 36, as shown in, for example, FIGS. 1, 3, 5, 6, 7, 8, 10 and 11. The wall holes 60 may be spaced substantially evenly about the perimeter/circumference 58 and substantially evenly about the sleeve length 44. The plurality of wall holes 60 are configured to allow vascularization (i.e., blood vessel growth and/or blood supply/flow growth) and tissue growth (i.e., the growth of collagen or 'scar tissue to secure the tissue 18 to the animal's bones beyond the fixation of the tissue 18 solely provided by the barbed sleeve 10 positioned in the bone hole 14).

Figure 16:
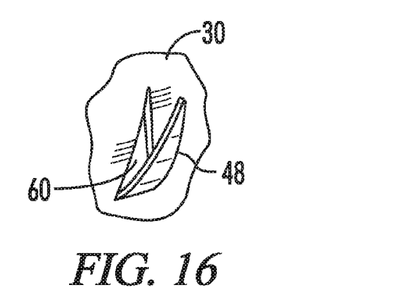
FIG. 16 illustrates a side, perspective view of a portion of a barbed sleeve of another embodiment of the present invention.

Optionally, each of the plurality of wall holes 60 are located directly next to an interior barb 48, each interior barb 48 is integral with the sleeve wall 30 and each wall hole 60 is substantially the same shape and size as the interior barb 48 directly next to the wall hole 60, as seen in FIG. 16. In other words, the interior barbs 48 are formed as cut-outs in the sleeve wall 30.

Optionally, the plurality of interior barbs 48 and the sleeve wall 30 are comprised of the same material.

Optionally, the plurality of interior barbs 48 are spaced substantially evenly about the sleeve length 44 and further wherein the plurality of interior barbs 48 are spaced radially substantially evenly about the barbed sleeve 10.

Optionally, the sleeve length 44 is from about 5 mm to about 50 mm and the sleeve width/diameter 46 is from about 5 mm to about 30 mm. It will be understood that such sizing is merely exemplary and other dimensions are possible.

Optionally, the sleeve length 44 is larger than the sleeve width/diameter 46. Optionally, the interior barbs 48 are angled between approximately 10 degrees and 80 degrees relative to the sleeve length/longitudinal axis 44, as denoted by the angle $\alpha$ in FIG. 15. Because the interior barbs 48 may be curved, the angle $\alpha$ mentioned above is determined by drawing a straight line from the front end 50 of a barb 48 to the rear end 52 of the barb 48.

Figure 14:
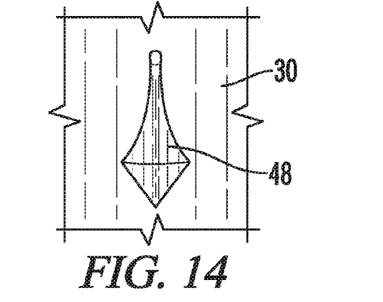
FIG. 14 illustrates a side elevation view of a portion of a barbed sleeve of another embodiment of the present invention.
Figure 17:
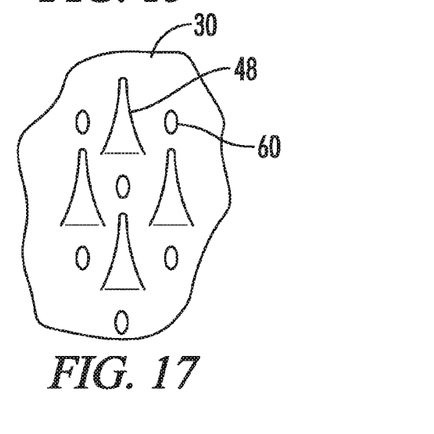
FIG. 17 illustrates a side, perspective view of a portion of a barbed sleeve of another embodiment of the present invention.

Optionally, the interior barbs 48 have an interior barb width 56 perpendicular to their length 54 and the rear ends 52 of the interior barbs 48 have a tapered width 56. In other words, the rear end 52 of each interior barb 48 may be narrower than the front end 50 of the same barb 48, as seen in FIGS. 14, 16 and 17 for example. Alternatively, the width 56 of the interior barbs 48 may be uniform along their lengths 54.

Figure 5:
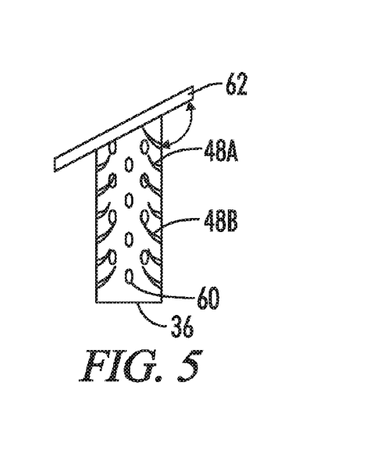
FIG. 5 illustrates a side elevation view of a barbed sleeve of another embodiment of the invention with an angled flange.
Figure 10:
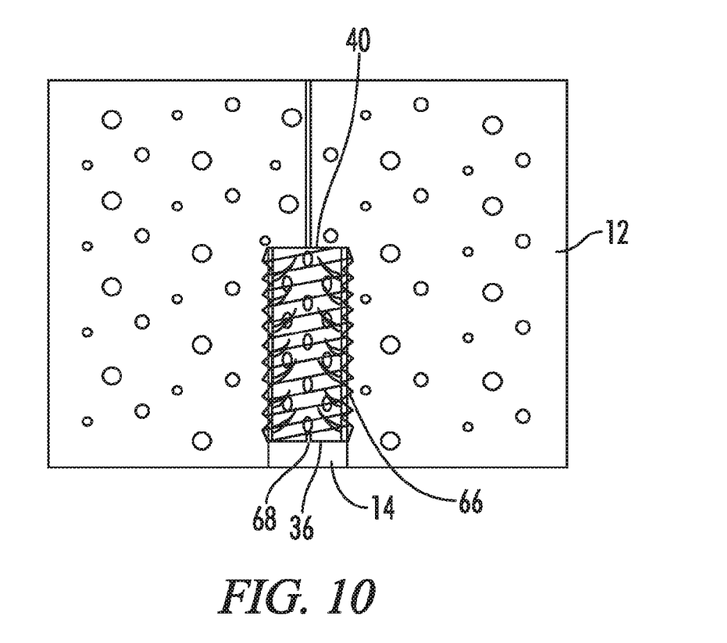
Figure 11:
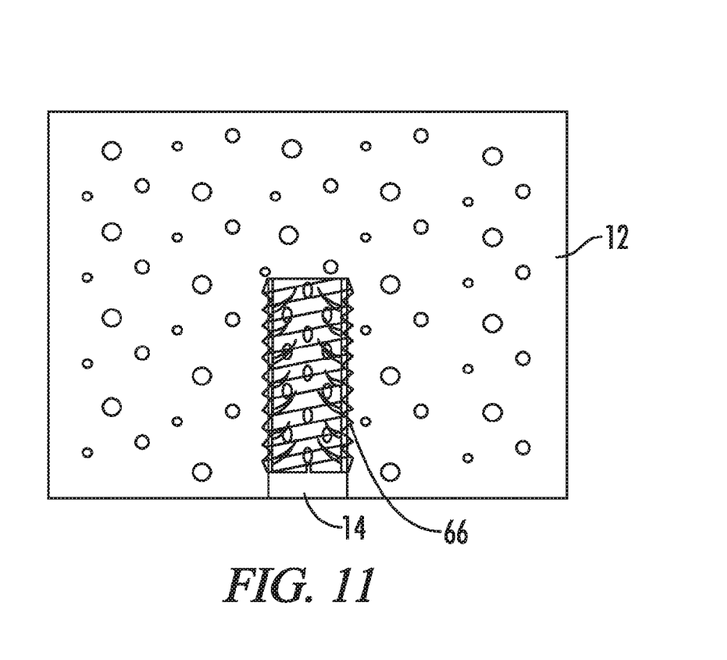
Figure 12:
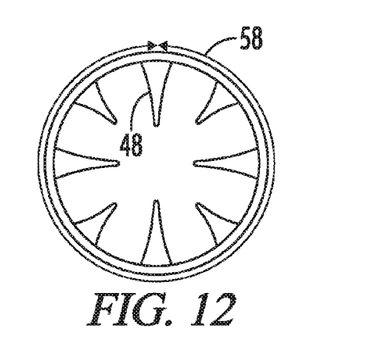
FIG. 12 illustrates a front, plan view of a barbed sleeve of another embodiment of the present invention.
Figure 13:
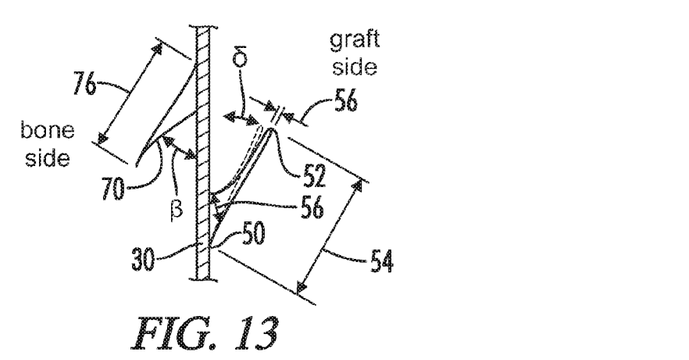
Figure 15:
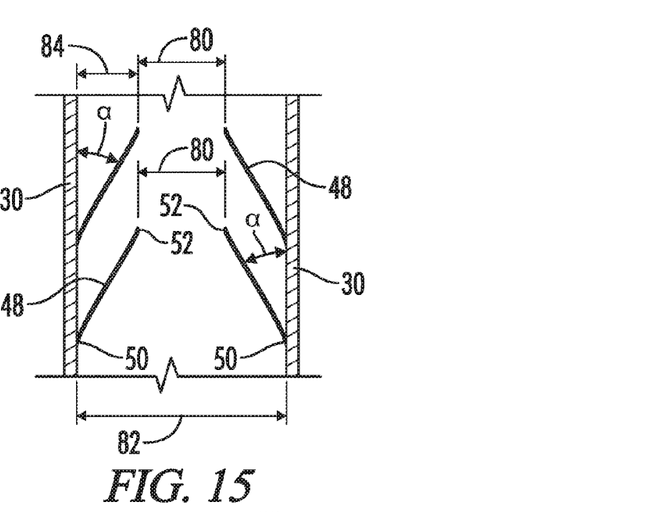

Optionally, the wall exterior surface 34 comprises a fastener configured to fix the barbed sleeve 10 relative to the bone 12. In some embodiments, the fastener is a flange 62 located adjacent to the sleeve rear end 40 that is configured to rest against the bone 12 and the flange 62 is configured to prevent the sleeve rear end 40 from moving through the hole 14 in the bone 12. For example, the flange width/diameter 64 may be larger than the width/diameter 16 of the bone hole 14, as shown in FIG. 6. Optionally, the flange diameter/width 64 is not perpendicular to the sleeve width/diameter 46 and further wherein the flange diameter/width 64 is not perpendicular to the sleeve length 44—i.e., the flange 62 is angled as shown in FIG. 5. In other embodiments, the fastener comprises threads 66 located on the wall exterior surface 34, as best seen in FIGS. 8, 10 and 11. If the fastener comprises threads 66, optionally, as shown in FIGS. 8-11, the sleeve front end 36 comprises at least one slot 68 and the method further comprises inserting a screwdriver into the at least one slot 68 and turning the screwdriver and the threads 66 (and the entire barbed sleeve 10) to fix the barbed sleeve 10 to the bone 12. In still further embodiments, as shown in FIGS. 1, 2, 13, the fastener comprises a plurality of exterior barbs 70 comprising a rear end 74 extending from the sleeve wall 30, a free front end 72 located in the sleeve exterior 29, and a length 76 extending from the front end 72 of the exterior barb 70 to the rear end 74 of the exterior barb 70. As shown in the drawings, preferably the front ends 72 of all of the exterior barbs 70 point in the same direction—i.e., towards the sleeve front end 36—and the rear end 74 of each exterior barb 70 (which extends from the wall 30) is located rearwardly relative to the front end 72 of the same exterior barb 70. In other words, the exterior barbs 70 point in the forward direction (opposite the interior barbs 48) and the exterior barbs 70 allow the barbed sleeve 10 to move rearwardly within the bone hole 14 (in the direction of the directional arrow in FIG. 1) but not forwardly within the bone hole 14 (i.e., opposite the direction of the directional arrow in FIG. 1). The exterior barbs 70 may be positioned similarly to the interior barbs 48 (e.g., spaced about the length 44 and about the perimeter/circumference 58), except that the exterior barbs 70 are in the sleeve exterior 29 and point toward the sleeve front end 36. When it is said that the front end 72 of the exterior barbs 70 point toward the sleeve front end 36, it will be understood that the front ends 72 of the exterior barbs 70 point both forwardly and laterally, given that the exterior barbs 70 may generally extend away from the sleeve wall 30 at an angle $\beta$, as shown in FIG. 15. Similarly, when it is said that the rear end 52 of the interior barbs 48 point toward the sleeve rear end 40, it will be understood that the rear ends 52 of the interior barbs 48 point rearwardly and laterally, given that the interior barbs 48 may generally extend away from the sleeve wall 30 at an angle $\alpha$, as shown in FIG. 15. In some embodiments, the front ends 72 of each exterior barb 70 move/deflect toward the sleeve wall 30 as the surgeon moves the sleeve 30 rearwardly within the bone hole 14. Optionally, the exterior barbs 70 purchase the bone 12 as the surgeon moves the sleeve 30 rearwardly within the bone hole 14.

Optionally, the bone hole 14 and the barbed sleeve 10 are generally cylindrical or oblong in shape. Optionally, if the barbed sleeve 10 includes threads 66, the bone hole width/diameter 16 is equal to or greater than the sleeve width/diameter 46 before inserting the sleeve 10 into the bone hole 14.

Optionally, at least some of the plurality of interior barbs 48 are curved. Optionally, at least some of the plurality of interior barbs 48 are straight. The exterior barbs 70 likewise may be curved or straight and may have alternating lengths 76 (i.e., short exterior barbs may be surrounded by longer exterior barbs, as described with the interior barbs 48A and 48B).

Optionally, the bone hole 14 extends partially through the bone 12 as seen in FIGS. 1, 8, 10, and 11. Optionally, the bone hole 14 extends completely through the bone 12, as seen in FIGS. 3, 6, and 7. It will be appreciated that if the barbed sleeve 10 includes a flange 62, the bone hole 14 may extend completely through the bone 12, while barbed sleeves 10 without the flange 62 may extend only partially through the bone 12. It will be understood that such preferences are exemplary and that other configurations are possible.

Optionally, the bone 12 forms part of a joint.

Example 1

A working prototype of a biocompatible barbed sleeve 10 was manufactured by laser cutting, forming and welding a nickel-titanium alloy tube. The barbed sleeve rear end 40 included a flange 62. The barbed sleeve 10 was cylindrical in shape and measured 10 mm in outer diameter 46, 8 mm in inner diameter 82, and 20 mm in length 44. The flange diameter 64 measured 14 mm in diameter and was perpendicular to the sleeve length 44. The barbed sleeve 10 consisted of sixty interior tapering barbs 48 that were 5 mm in length 54 and 1 mm in maximum width 56. (By tapering, it is meant that the widths 56 were tapered as discussed previously—i.e., the rear end 52 of each interior barb 48 was narrower than the front end 50 of the same barb 48, as seen in FIGS. 14, 16 and 17 for example). The interior barbs 48 were spaced substantially equally about the circumference 58 of the barbed sleeve 10 and substantially equally about the sleeve length 44. The interior barbs 48 were angled approximately 25 degrees relative to the sleeve length 44—i.e., a was approximately 25 degrees. The rear ends 52 of the interior barbs 48 pointed toward the sleeve rear end 40 and were located in the sleeve interior 28 as seen in FIGS. 3 and 6 for example. The rear ends 52 of the interior barbs 48 protruded inwardly a distance 84 of 2 to 2.2 mm such that the space between the rear ends 52 of diametrically opposed interior barbs 48 had a width/diameter 80 of about 3.6 mm to about 4 mm. The barbed sleeve 10 included sixty wall holes 60 which were 1.5 mm in diameter and were spaced substantially evenly about the sleeve circumference 58 and substantially evenly about the sleeve length 44. The barbed sleeve 10 was placed within a 10 mm cylindrical hole within a base block (thus the 10 mm hole simulated the bone hole 14 and the base block simulated the bone 12) such that the flange 62 was seated against the surface of the base block providing a point of fixation, similar to the setup shown seen in FIG. 6. Human tendon allograft 18 of 8 mm diameter 23 was held with suture 26 and advanced into the base block rearwardly and upwardly as seen in FIG. 6. The interior barbs 48 allowed unidirectional passage of the allograft 18 rearwardly through the barbed sleeve interior 28, whereas the interior barbs 48 purchased the allograft 18 and prevented forward movement of the allograft 18, as seen in FIG. 7. The front end 20 of the allograft 18 was serially tensioned with incremental mass to assess both the fixation of the barbed sleeve 10 to the base block and fixation of the allograft 18 to the barbed sleeve 10 (i.e., weights were hung from the front end 20 of the allograft). The barbed sleeve 10 was tested utilizing three allograft specimen 18. The barbed sleeve 10 succeeded in maintaining fixation at both the interface of the barbed sleeve 10 and the base block and the interface of the barbed sleeve 10 and the allograft 18 to over 75 pounds. Ultimate failure occurred away from the barbed sleeve 10 at the front end 20 of the allograft 18 where the allograft 18 failed at the point of fixation to the incremental mass. Inspection of the barbed sleeve 10 upon completion of testing revealed no failure or deformation of the barbed sleeve 10 or the interior barbs 48.

The barbed sleeve 10 may be used in a variety of surgeries, including without limitation, shoulder (AC separation [acromioclavicular ligament reconstruction, bicep tendon repair), elbow (tendon repair, ligament reconstruction —Tommy John procedure in pitchers), wrist (tendon repair or transfer), hand (tendon repair), hip (hamstring repair), knee (ACL/PCL reconstruction, collateral ligament repair or reconstruction, patellofemoral ligament reconstruction), ankle (tendon repair or transfer, ligament repair or reconstruction), and foot (tendon repair).

Having now described the invention in accordance with the requirements of the patent statutes, those skilled in the art will understand how to make changes and modifications to the disclosed embodiments to meet their specific requirements or conditions. Changes and modifications may be made without departing from the scope and spirit of the invention. In addition, the steps of any method described herein may be performed in any suitable order and steps may be performed simultaneously if needed.

Terms of degree such as "generally", "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

What is claimed is:
1. A method of attaching a soft tissue to a bone of an animal comprising:
 a) creating a hole in a bone;
 b) providing a tubular barbed sleeve comprising a sleeve interior, a sleeve exterior, a sleeve wall separating the sleeve interior from the sleeve exterior and comprising a wall interior surface facing the sleeve interior and a wall exterior surface, a sleeve front end comprising a sleeve front opening leading to the sleeve interior, a sleeve rear end comprising a sleeve rear opening leading to the sleeve interior, a sleeve length extending from the sleeve front end to the sleeve rear end, a sleeve width perpendicular to the sleeve length, a plurality of interior barbs coupled to the sleeve wall, each interior barb comprising a barb front end extending from the sleeve wall, a free barb rear end located in the sleeve interior and rearwardly disposed relative to the barb front end, and a barb length extending from the barb front end to the barb rear end, wherein the barbed sleeve is comprised of a biocompatible material;
 c) positioning the barbed sleeve into the hole in the bone;
 d) providing a soft tissue having a tissue front portion and a tissue rear portion;

e) after step c), unidirectionally securing the tissue rear portion in the sleeve interior while the barbed sleeve is positioned within the hole in the bone, wherein the unidirectional securing comprises positioning the tissue rear portion through the sleeve front end and into the sleeve interior such that at least one of the plurality of interior barbs contacts the soft tissue, wherein the plurality of interior barbs allows the soft tissue to move rearwardly within the sleeve interior, but prevents the soft tissue from moving forwardly within the sleeve interior, and wherein each of the interior barbs is located fully within the sleeve interior after step e).

2. The method of claim 1, wherein, prior to positioning the soft tissue into the sleeve interior, the soft tissue comprises a tissue length extending from the tissue front portion to the tissue rear portion and a tissue width perpendicular to the tissue length, wherein said plurality of interior barbs comprise at least one pair of interior barbs whose rear ends are located approximately 180 degrees apart and at approximately the same distance from the sleeve front end and further wherein said rear ends of said at least one pair create a space that has a width that is less than the tissue width.

3. The method of claim 1, wherein the method further comprises attaching the tissue front portion to a body part of the animal.

4. The method of claim 1, wherein the interior barbs are spaced about a perimeter of the sleeve interior and about the sleeve length and further wherein at least a majority of the barbed sleeve length is located in the bone during step e).

5. The method of claim 1, wherein the barbed sleeve is oblong in shape.

6. The method of claim 1, wherein the sleeve wall comprises a plurality of wall holes extending from the wall interior surface to the wall exterior surface, the plurality of wall holes spaced about a perimeter of the sleeve interior and about the sleeve length and configured to allow vascularization and tissue growth.

7. The method of claim 1, wherein the sleeve width is not tapered along the sleeve length.

8. The method of claim 1, wherein each interior barb has a barb width perpendicular to the barb length and further wherein the barb rear ends have a tapered width.

9. The method of claim 1, wherein the wall exterior surface comprises a fastener configured to fix the barbed sleeve relative to the bone.

10. The method of claim 9 wherein the fastener is a flange located adjacent to the sleeve rear end and further wherein after step c), the flange contacts a surface of the bone and prevents the sleeve rear end from moving through the hole in the bone, wherein the bone hole comprises a first end and a second end opposite the first end, wherein step c) comprises inserting the sleeve front end through the first end of the bone hole and step e) comprises inserting the tissue rear portion into the second end of the bone hole.

11. The method of claim 10 wherein the flange comprises a flange width, and further wherein the flange width is not perpendicular to the sleeve width and further wherein the flange width is not perpendicular to the sleeve length.

12. The method of claim 9 wherein the fastener comprises threads located on the wall exterior surface.

13. The method of claim 12 wherein the sleeve front end comprises at least one slot and the method further comprises inserting a screwdriver into the at least one slot and turning the screwdriver and the barbed sleeve to fix the barbed sleeve to the bone.

14. The method of claim 9 wherein the fastener comprises a plurality of exterior barbs coupled to the sleeve wall, each exterior barb comprising an exterior barb rear end extending from the sleeve wall, a free exterior barb front end located in the sleeve exterior and forwardly disposed relative to the exterior barb rear end, and a length extending from the exterior barb front end to the exterior barb rear end.

* * * * *